United States Patent [19]

Redmond et al.

[11] Patent Number: 5,503,833
[45] Date of Patent: Apr. 2, 1996

[54] VP6 ENCAPSULATED DRUG DELIVERY

[75] Inventors: Mark J. Redmond; Manuel Campos, both of Saskatoon, Canada

[73] Assignee: University of Saskatchewan, Saskatoon, Canada

[21] Appl. No.: 301,267

[22] Filed: Sep. 6, 1994

Related U.S. Application Data

[63] Continuation of Ser. No. 825,522, Jan. 29, 1992, abandoned, which is a continuation-in-part of Ser. No. 650,054, Feb. 4, 1991, abandoned.

[51] Int. Cl.$^6$ .......................... C07K 16/00; A61K 39/15; A61K 39/385; A61K 45/05
[52] U.S. Cl. .................... 424/196.11; 424/193.1; 424/281.1; 424/450; 424/215.1; 424/852; 424/85.5; 514/12; 530/391.1
[58] Field of Search ................... 530/391.1; 424/85.5, 424/85.2, 196.11, 215.1, 281.1, 450, 499, 193.1, 391.1; 514/12

[56] References Cited

U.S. PATENT DOCUMENTS

| 4,650,674 | 3/1987 | Aggarwal et al. | 424/85.1 |
|---|---|---|---|
| 4,863,726 | 9/1989 | Stevens et al. | 424/85.2 |
| 5,071,651 | 12/1991 | Sabara et al. | 424/215.1 |

FOREIGN PATENT DOCUMENTS

| 0235391 | 9/1987 | European Pat. Off. . |
|---|---|---|
| 0251631 | 1/1988 | European Pat. Off. . |
| 0273366 | 7/1988 | European Pat. Off. . |
| 0305967 | 3/1989 | European Pat. Off. . |
| 2146525 | 4/1985 | United Kingdom . |

OTHER PUBLICATIONS

Gewgoriadis, *Liposome Technology* (1984) 1:17–30 (CRC Press, Boca Raton, Fla.).
Gregoriadis, *Trends in Biotechnology (1985) 3(9):235–241.*
Fidler et al., *Cancer Res.* (1982) 42:496–501.
Straubinger et al., *Cancer Res.* (1988) 48:5237–5245.
Koff et al., *Infection and Immunity* (1983) 42:1067–1072.
Redmond et al., *Mol. Immunol.* (1990) 28(3):269–278 )Pre--print enclosed herewith).
Almeida et al., *J. Med. Virol.* (1979) 4:269–277.
Bican et al., *J. Virol.* (1982)43:1113–1117.
Gorziglia et al., *J. Gen. Virol.* (1985) 66:1889–1900 (abstract enclosed herewith).
Ready et al., *Virology* (1987) 157:189–198.
Estes et al., *J. Virol.* (1987) 61:1488–1494.
Both et al., *J. Virol.* (1984) 51:97–101 (abstract enclosed herewith).
Cohen et al., *Virology* (1984() 138:178–182.
*Animal Pharm.* (Aug. 4, 1989) 185:13.
Ratafla et al, *New Biotech. Business* 2(8):3–7.
Sandino et al., *J. Virol.* (1986) 60(2):797–802.

*Primary Examiner*—Lila Feisee
*Attorney, Agent, or Firm*—Morrison & Foerster

[57] ABSTRACT

Compositions and methods for preparing and delivering encapsulated biologically active agents to specific cell types are disclosed. Substances can be encapsulated in the VP6 inner capsid protein of rotavirus and delivered to selected cells, tissues and organs. Targeting agents can be linked to the surface of the VP6 sphere so that appropriate agents can be delivered to preselected cells and tissue types.

3 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Cys Asp Gly Lys Tyr Phe Ala Tyr Lys Val Glu Thr Ile Leu Lys Arg
1               5                   10                  15

Phe His Ser Met Tyr Gly (2) INFORMATION FOR SEQ ID NO:2:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Cys  Asn  Ile  Ala  Pro  Ala  Ser  Ile  Val  Ser  Arg  Asn  Ile  Val  Tyr  Thr
 1              5                             10                       15

Arg  Ala  Gln  Pro  Asn  Gln  Asp  Ile  Ala
              20                        25
```

VP6 ENCAPSULATED DRUG DELIVERY

CROSS-REFERENCE TO RELATED APPLICATIONS

This application is a a continuation of U.S. application Ser. No. 07/825,522, filed 29 Jan. 1992, now abandoned which is a continuation-in-part of U.S. application Ser. No. 07/650,054, filed 4 Feb. 1991, now abandoned from which priority is claimed under 35 USC § 120 and which is incorporated herein by reference in its entirety.

DESCRIPTION

1. Technical Field

The instant invention relates generally to novel drug targeting and delivery methods. More particularly, the present invention relates to the application of rotavirus VP6 spheres to the delivery of drugs.

2. Background

Recent advances in biotechnology have permitted the development of new approaches for preparing and delivering therapeutic and diagnostic agents. Of particular importance is the ability to target drugs and other agents to tissues, cells or subcellular organelles using carrier systems in order to improve drug selectivity and reduce toxicity. Systems currently in use employ macromolecules, synthetic polymers and particles to achieve this end. However, most systems are limited by the quantity and range of drugs that can be incorporated into the complex as well as the inability of the drug to target and act on selected cells. Furthermore, the carrier often includes toxic components and technical problems can be encountered in the preparation of the drug-carrier complex.

One method of delivering therapeutic substances involves the use of a drug or cytotoxic agent conjugated to a cell-specific antibody to form an immunoconjugate. The conjugate binds cells having a surface antigen against which the antibody is directed. However, these delivery systems suffer from several drawbacks. Oftentimes, large quantities of drug must be delivered to the target cell in order to achieve the desired response. Such large amounts are often unobtainable due to the limited number of cell surface antigens and the number of drug molecules that can be attached to any given antibody. Furthermore, the cytotoxic activity of an immunoconjugate is often dependent on its uptake and internalization by the target cell. However, most immunoconjugates are not internalized and if internalized, the drug or cytotoxic agent is often degraded by the lysosome of the cell. Finally, cells, such as tumor cells, are often heterogeneous with respect to antigen expression and antigen-positive cells may give rise to antigen-negative progeny. Therefore, in a given population of tumor cells, there will be a certain number of cells that lack the antigen for which a particular immunoconjugate is specific.

Protein microspheres have also been used to administer drugs. These microspheres are formed by combining the particular therapeutic agent with the carrier protein and mixing the complex with oil to form micelles. These micelles are stabilized using chemical cross-linking agents. However, the final stabilization step can inactivate the drug.

Liposomes have been employed in an effort to overcome these problems. Liposomes are microscopic vesicles formed from natural lipid constituents such as phospholipids. Pharmacologically active agents can be entrapped in the liposomes for subsequent delivery. For a general review of liposome technology see Gregoriadis, G., *Liposome Technology* (CRC Press, Roca Baton, Fla., 1984); Gregoriadis, *Trends in Biotechnology* (1985) 3:235.

Several experimenters have suggested the use of liposomes for the delivery of antitumor and antiviral agents. For example, Fidler et al., *Cancer Research (*1982) 42:496–501 describes the use of liposome encapsulated lymphokines of muramyl dipeptide (MDP) to activate host macrophages which in turn destroy lung and lymph node metastases.

Straubinger et al., *Cancer Research* (1988) 48:5237–5245 examines the in vitro cytotoxicity of liposome encapsulated methotrexate-σ-aspartate and 5-fluoroorotate to a human ovarian cancer cell line and discloses that the encapsulation of these drugs in liposomes allows the intracellular delivery of the drugs into cells.

Koff et al., *Infection and Immunity* (1983) 42:1067–1072 describes the use of liposome encapsulated macrophage activating factor for the activation of macrophages against HSV-2 infected cells.

U.K. Patent Application No. GB 2,146,525 A describes the use of liposomes with porphyrins bound to the outermost layer. The liposomes carry anticancer drugs and macrophage activating factors.

Finally, U.S. Pat. No. 4,650,674 describes synergistic compositions including an interferon and tumor necrosis factor and discloses that the composition can be encapsulated in liposomes for injection directly into the tumor.

Although the use of liposomes as a drug delivery system alleviates some of the problems described above, this drug delivery technique suffers from several drawbacks. Specifically, effective means to target liposomes to the desired site of drug action is lacking. Furthermore, liposomes exhibit poor stability during storage and use and there are problems with the large scale production and manufacturing of liposomes. In an attempt to overcome these problems, experimentors have delivered substances using viral particles. For example, WO 91/06658, published 16 May 1991, describes the use of retroviral vectors carrying RNA sequences that encode tumor necrosis factor, interleukin-2 and multiple drug resistance proteins.

The inner capsid of rotavirus includes at least three proteins designated VP1, VP2 and VP6. Of interest herein is VP6 which is a 45 kD protein. VP6 is an effective carrier protein for haptens or antigens attached to its surface. See, U.S. Pat. No. 5,071,651, incorporated herein by reference in its entirety. Protein, peptide and carbohydrate antigens can be coupled to the surface of the VP6 protein through binding peptides or chemical reactions. The VP6 carrier finds use as an antigen presentation system for the delivery of antigens to the immune system to elicit an antibody response.

However, antigen delivery may be limited by the size of the bound substance and it may be undesirable to place some molecules on the surface of the VP6 sphere, such as those that would target all cells having a receptor thereto. Thus, encapsulation of a desired substance could overcome this lack of selectivity. The present invention provides a means for encapsulating therapeutic agents within VP6 spheres in order to achieve more efficient delivery to cells, cellular organelles, and organs.

SUMMARY OF THE INVENTION

The instant invention is based on the discovery that VP6 rapidly targets, attaches to and is engulfed by monocytes and macrophages. Redmond, M. J., et al., *Mol Immunol* (1991)

28(3):269–278. The present invention is also based on the discovery that the VP6 inner capsid protein of rotavirus can be used to encapsulate therapeutic agents. Thus, substances to be delivered to target cells can be encapsulated in VP6 spheres to effect an increase in the concentration of the agent delivered to the cells. Additionally, other targeting agents can be attached to the VP6 spheres that will direct the spheres to other tissues and cell types so that biologically active agents encapsulated within the spheres can act locally.

Accordingly, in one embodiment, the instant invention is directed to a composition capable of delivering a biologically active agent to a target. The composition comprises a biologically active agent encapsulated in VP6 protein. A targeting agent can be present on the surface of the spheres to direct the composition to a particular cell type.

In another embodiment, the subject invention is directed to a method for encapsulating a biologically active agent in VP6 protein spheres which comprises:

(a) mixing unassembled VP6 protein with said biologically active agent; and (b) effecting the formation of assembled VP6 protein spheres thereby encapsulating said biologically active agent.

In yet another embodiment, the subject invention relates to a method of delivering a biologically active agent to a selected group of cells in a mixture of cells. The method comprises combining the mixture of cells with the compositions described above.

These and other embodiments of the present invention will readily occur to those of ordinary skill in the art in view of the disclosure herein.

DETAILED DESCRIPTION

The practice of the present invention will employ, unless otherwise indicated, conventional techniques of immunology, protein chemistry, molecular biology, microbiology and recombinant DNA technology, which are within the skill of the art. Such techniques are explained fully in the literature. See, e.g., *Handbook of Experimental Immunology*, Vols. I–IV (D. M. Weir and C. C. Blackwell eds., 1986, Blackwell Scientific Publications); *Methods in Enzymology* (S. Colowick and N. Kaplan eds., Academic Press, Inc.); Sambrook, Fritsch & Maniatis, *Molecular Cloning: A Laboratory Manual,* 2d Edition (Cold Spring Harbor Laboratory Press, 1989); *Oligonucleotide Synthesis* (M. J. Gait ed., 1984); and *DNA Cloning,* Volumes I and II (D. N. Glover, ed., 1985).

All patents, patent applications, and publications mentioned herein, whether supra or infra, are hereby incorporated by reference.

A. Definitions

In describing the present invention, the following terms will be employed, and are intended to be defined as indicated below.

By "VP6 protein" is meant the art-recognized major viral protein of the inner capsid from any species or strain within the family Reoviridae or a protein functionally equivalent or substantially homologous thereto, as defined below. See, e.g., Kapikian, et al., in *Virology* (B. N. Fields et al., eds., 1988). Examples of rotavirus strains from which the VP6 protein can be isolated and employed in the present invention include, but are not limited to, Simian SA11, human D rotavirus, bovine UK rotavirus, human Wa or W rotavirus, human DS1 rotavirus, rhesus rotavirus, the "0" agent, bovine NCDV rotavirus, human S2 rotavirus, human KUN rotavirus, human 390 rotavirus, human P rotavirus, human M rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU1 rotavirus, feline Taka rotavirus, equine H2 rotavirus, human St. Thomas No. 3 and No. 4 rotaviruses, human Hosokawa rotavirus, human Hochi rotavirus, porcine SB2 rotavirus, porcine Gottfried rotavirus, porcine SB1A rotavirus, porcine OSU rotavirus, equine H1 rotavirus, chicken Ch.2 rotavirus, turkey Ty.1 rotavirus, bovine C486 rotavirus, and strains derived therefrom. Thus VP6 protein for use in the present invention includes VP6 from any rotavirus strain, whether from subgroup I, subgroup II, or any as yet unidentified subgroup, as well as from any of the serotypes 1–7, as well as any as yet unidentified serotypes. It is to be understood that VP6 protein for use in the present invention may be recombinantly produced based on the sequences of these isolated proteins.

The nucleotide sequence encoding VP6 and amino acid sequence of VP6 is known for several different strains of rotavirus. Extensive homology is present between strains.

Two DNA or protein sequences are "substantially homologous" when at least about 85% (preferably at least about 90%, and most preferably at least about 95%) of the nucleotides or amino acids match over a defined length of the molecule.

The term "functionally equivalent" refers to sequences of an analog of VP6 protein which define a chain that will produce a protein capable of encapsulating a biologically active agent and delivering that agent to the desired target cell type in an equivalent manner as the native sequence. Assays for determining such functional equivalents are described herein and are well known in the art. Thus, the VP6 proteins utilized herein need not have the identical amino acid sequence of the native proteins.

By "exerting an effect on a selected group of cells" is generally meant either activating or inactivating specific cells, retarding or halting cell growth or differentiation, actively killing particular cells or bacteria, virus, fungi or parasites within cells, or mutagenizing the genetic material within cells, or all of the above. The effect will vary depending on the biologically active agent present and the cells targeted. For example, if cytokines are encapsulated in the VP6 spheres, monocytes and macrophages, the natural targets of VP6, will be activated and phagocytic cell function enhanced. Thus, the immune system in a subject administered the compositions of the present invention will be stimulated. This, in turn, can act to fight viral, bacterial, parasitic and fungal infections, as well as retard or halt tumor cell growth or otherwise alter immune function. If other targeting agents are present on the VP6 sphere, such as an antibody reactive with an antigen found on a tumor cell surface, and a cytotoxic agent is encapsulated within the VP6 sphere, the cytotoxic agent can be delivered directly to the cancerous cells. The effect contemplated is a cytotoxic effect that will either arrest or diminish tumor cell growth. Additionally, specific tissues and cell types, such as liver, spleen, heart, kidney, lung, intestinal cells, erythrocytes, or other cells of the hematopoietic-immune system, such as T cells, B cells, bone marrow and other progenitor cells, monocytes, maerophages, natural killer cells or neutrophils, can be selected and targeted to by linking agents such as viral proteins, and the like, known to migrate to these cells, on the VP6 sphere. One effect of such targeting is to prime the local immune system to alleviate infection at the particular cell site. Other local responses are also contemplated, as discussed above.

It is readily apparent from the above discussion that "a selected group of cells" or a "target" encompasses several cell types including cells of the hematopoietic-immune system such as monocytes, macrophages, T cells, and neutrophils, as well as tumor cells, or other specific organs, cell types or tissues, such as liver cells or intestinal mucosal cells. Furthermore, the "selected group of cells" with which the encapsulated substance is combined and acts can be present in a mixed cell population either in vitro or in vivo.

A "biologically active agent" is one which is capable of exerting an effect as described above.

By "delivery to a target" is meant the delivery of the encapsulated agent to a target cell or tissue as described above, where the agent can act locally. Depending on the nature of the therapeutic agent and/or any targeting moiety linked to the VP6 sphere, the agent will either react directly with cell surface receptors or be internalized by the target cell or tissue.

By "encapsulated" is meant the entrapment of the biologically active agent within the VP6 spheres. Specifically, a spherical particle is formed around the desired substance. Unlike previous carrier systems using VP6 to deliver surface antigens, the instant invention does not depend on linking sequences or protein-protein interactions to "hook" the active agent to receptors on the VP6 molecule. Thus, the term "encapsulated" does not contemplate systems wherein the active substance is bound to the VP6 protein receptors via these mechanisms.

The terms "polypeptide" and "protein" are used interchangeably herein and are used in their broadest sense, i.e., to denote any polymer of amino acids (dipeptide or greater) linked through peptide bonds. Thus, the terms encompass oligopeptides, protein fragments, analogs, mutants, fusion proteins and the like.

"Native" proteins or polypeptides refer to proteins or polypeptides recovered from rotavirus or from rotavirus infected cells. Thus the term includes naturally occurring rotavirus proteins and fragments thereof. "Non-native" polypeptides refer to polypeptides that have been produced by recombinant DNA methods or by direct synthesis. "Recombinant" polypeptides refer to polypeptides produced by recombinant DNA techniques; i.e., produced from cells transformed by an exogenous DNA construct encoding the desired polypeptide.

A composition containing A is "substantially free of" B when at least about 85% by weight of the total of A+ B in the composition is A. Preferably, A comprises at least about 90% by weight of the total of A+ B in the composition, more preferably at least about 95%, or even 99% by weight.

B. General Methods

Central to the instant invention is the discovery that a variety of substances can be encapsulated in rotavirus VP6 spheres. Encapsulation is achieved in a simple reaction which requires little time and allows a wide range of agents to be incorporated in the VP6 protein. The instant invention does not require the use of linking agents or protein-protein interactions since the therapeutic agent is actually encapsulated within the interior of the sphere rather than linked to the VP6 surface receptors. In this way, a larger variety of substances can be efficiently delivered using the VP6 spheres.

Biologically active agents which can be encapsulated in the VP6 spheres include but are not limited to cytokines such as interferon (IFN) alpha, beta and gamma; colony stimulating factors such as granulocyte-macrophage CSF (CSF-GM), macrophage CSF (CSF-M), neutrophilic granulocyte CSF (CSF-G), BPA, multi-CSF, HCGF, MCGF, and PSF (see, e.g., Metcalf *Science* (1985) 229:16), primitive cell colony stimulating factor (CSF-PC), macrophage inflammatory factor, tumor necrosis factor (TNF); and interleukins such as IL-1, IL-2, IL-3, IL-4, IL-5, IL-6, IL-7, IL-8, IL-9, IL-10, IL-11 (see, e.g. *Ann. Rev. Immunol.* Vols. 1–8). The instant invention is particularly useful for delivering poorly soluble molecules such as recombinantly produced cytokines. Encapsulation of these agents in VP6 overcomes this problem.

Many other molecules are known in the art which will find use when encapsulated in the VP6 protein. Examples of the classes of such molecules, usually macromolecules, are polypeptides, carbohydrates, nucleic acids including nucleotide and nucleoside analogs. Proteins, glycoproteins, and peptides can include hormones, glucagon, insulin-like growth factors, growth hormone, thyroid stimulating hormone, prolactin, inhibin, secretin, neurotensin, cholecystokinin or fragments thereof, calcitonin, somatostatin, thymic hormones, neurotransmitters and blockers, peptide-releasing factors (e.g., enkephalins), growth hormone releasing factor, as well as fragments of proteins, such as calmodulin, *E. coli* heat stable and heat labile enterotoxin, cholera toxin; and enzymes, such as protein kinase of Rous sarcoma virus. Additional substances include steroid hormones, such as testosterone, estradiol, aldosterone, endorostenedione, or fragments thereof. Examples of nucleotides include polynucleotide fragments, restriction enzyme sites, and cyclic nucleotides (e.g., cyclic adenosine monophosphate). Examples of carbohydrates and carbohydrate complexes include bacterial capsules or exopolysaccharides (e.g., from Hemophilus influenzae B), bacterial lipid A associated core antigens (e.g., from Pseudomonas species), blood group antigens (e.g., the ABO antigens), and glycolipids. Examples of lipids include fatty acids, glycerol derivatives, prostaglandins (e.g., prostaglandin $E_2$), and lipopeptides (e.g., leukoteiene $B_4$). Molecules of interest can also include alkaloids, such as vindoline, serpentine, catharanthine, as well as vitamins containing —OH, NH, SH, CHO, or COOH functional groups.

A wide variety of therapeutic agents including cytotoxic agents, mutagens, antibacterial, antiviral, antifungal and antiparasitic agents will also find use in the instant invention, including but not limited to such drugs as ricin, cyclosporin A, streptomycin, amphotericin B, aflatoxin vincristine, doxorubicin, propranolol,, porphyrins, acyclovir and AZT.

The amount and type of substance which can be effectively encapsulated in the VP6 sphere is determined in part by the size of the VP6 sphere, in part by the physical and chemical make-up of the VP6 sphere, and in part by the characteristics of the substance to be encapsulated therein. Specifically, the diameter of the VP6 particle is approximately 70 μm, with a maximum volume of $1.8 \times 10^{-22}$ m$^3$. The surface of the sphere appears to be perforated by 132 channels, 40–65 angstroms in diameter (Jeager et al., *J. Cell Biol.* (1990) 110:2133–2144). Therefore, while molecules having cross sections smaller than about 20 angstroms may leak from the sphere, different molecules will leak at different rates. Thus, small molecules which are retained in sufficient amounts for effective delivery, will find use with the instant invention. Furthermore, certain smaller molecules are also retained within the sphere due to hydrophobic interactions between the molecules and perforated surfaces. Thus, generally, substances having a molecular mass of at least about 200 daltons, preferably about 500 daltons, and most preferably about 10,000 daltons, will find use in the instant invention. However, other agents falling outside of these boundaries will also be capable of encapsulation if the proper hydrophobic properties are present. Alternatively, small molecules can be polymerized or complexed to higher molecular weight molecules, such as BSA, to insure their retention in the VP6 sphere. One of ordinary skill in the art can readily determine whether a particular substance can be effectively encapsulated in view of the examples herein.

The VP6 protein for use in the instant invention can be prepared by any of several methods. First, the VP6 protein can be isolated from in vitro derived single-shelled virus particles by calcium chloride ($CaCl_2$) or lithium chloride (LiCl) treatment by standard techniques. See, e.g., Almeida et al., *J Med Virol* (1979) 4:269–277; Bican et al., *J Virol* (1982) 43:1113–1117; Gorziglia et al., *J Gen Virol.* (1985) 66:1889–1900; Ready et al., *Virology* (1987) 157:189–198. Alternatively, the VP6 protein can be produced by recombinant DNA techniques, which are fully explained in the literature. See, e.g., Sambrook et al., supra; and *DNA Cloning,* supra.

DNA coding sequences encoding the VP6 polypeptide can be derived from VP6 mRNA. See, e.g., Estes et al., supra; Both et al., *J Virol* (1984) 51:97–101; Cohen et al., *Virology* (1984) 138:178–182. Alternatively, a DNA sequence encoding the VP6 protein can be prepared synthetically rather than cloned. The DNA sequence can be designed with the appropriate codons for the viral protein amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J Biol Chem* (1984) 259:6311.

Once a coding sequence for the viral protein has been prepared or isolated, it can be cloned into any suitable vector or replicon. Numerous cloning vectors are known to those of skill in the art, and the selection of an appropriate cloning vector is a matter of choice. Examples of recombinant DNA vectors for cloning and host cells which they can transform (in parenthesis) include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See generally, *DNA Cloning:* Vols. I & II, supra; and Sambrook et al., supra.

The coding sequence for the VP6 protein can be placed under the control of a promoter, ribosome binding site (for bacterial expression) and, optionally, an operator (collectively referred to herein as "control" elements), so that the DNA sequence encoding the VP6 protein is transcribed into RNA in the host cell transformed by a vector containing this expression construction. The coding sequence may or may not contain a signal peptide or leader sequence. In bacteria, for example, the viral protein is preferably made by the expression of a coding sequence containing a leader sequence which is removed by the bacterial host in post-translational processing. See, e.g., U.S. Pat. Nos. 4,431,739; 4,425,437; 4,338,397.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also UK Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; and 96,491.

Particularly useful for expression of the VP6 protein of the instant invention are insect cells and vectors suitable for use in these cells. Such systems are known in the art, and include, for example, insect expression transfer vectors constructed from the baculovirus *Autographa californica* nuclear polyhedrosis virus (AcNPV). Such expression vectors typically use the strong viral polyhedrin gene promoter to control expression of heterologous genes. Methods for the introduction of heterologous DNA into the desired site in the baculovirus are known in the art. (See, e.g. Smith, et al., *Mol and Cell Biol* (1983) 3:2156–2165; Luckow and Sumners *Virology* (1989) 17:31; Estes, et al., *J Virol* (1987) 61:1488–1494 and European Patent Application 273,366. Insertion can be, for example, into a gene such as the polyhedrin gene, by homologous recombination. Insertion can also be into a restriction enzyme site engineered into the desired baculovirus gene. Sequences encoding signal peptides can also be used in these expression systems since these peptides are recognized by insect cells and will cause the secretion of the expressed product into the expression medium.

Depending on the expression system and host selected, the viral protein is produced by growing host cells transformed by an expression vector described above under conditions whereby the protein is expressed. The protein is then isolated from the host cells and purified. If the expression system secretes the protein into growth media, the protein can be purified directly from cell-free media. If the protein is not secreted, it is isolated from cell lysates. The selection of the appropriate growth conditions and recovery methods are within the skill of the art.

Purified VP6 protein exhibits structural polymorphism. Specifically, hexamers and small hexagonal lattices are present in many of the samples. Tubular particles form between about pH 5.0 and about pH 9.0, and are moderately stable to changes in temperature and ionic strength. The formation of these particles is fully reversible. Spherical particles reassembling single-shelled virus can be formed at about pH 4.0. A novel structure, in the form of sheets, composed of small-hole lattice, is formed in samples shifted from about pH 6.0 to about pH 4.0. These results demonstrate the importance of protein-protein interactions for rotavirus assembly.

Such protein-protein interactions are likely involved in the observed phenomenon that certain peptides can bind to VP6 in its monomeric form or to various oligomeric structures formed from VP6 monomers, such as in vitro assembled tubes and spheres. The attachment is mediated by a specific binding site(s) within VP6.

After the VP6 protein has been either isolated, synthesized, or recombinantly produced, the unassembled protein is combined in a simple reaction with the desired therapeutic agent and a sphericle particle is formed around the agent. Generally, the reaction involves mixing the therapeutic agent with a VP6 preparation at a pH outside of the pH range that spherical particles are formed. Particles resembling single-shelled virus can be formed at about pH 4.0 or higher. Thus, the agent to be encapsulated can be added to a VP6 preparation at a pH either below or equal to about pH 4.0. The pH of the solution is then changed to about pH 4.0 or greater using any suitable means, such as buffer exchange or dialysis. Any agent remaining outside the spheres may be separated from the particles by simple purification techniques, such as centrifugation or ultrafiltration. The free material may be used in additional encapsulation cycles.

Specific targeting agents can be linked to the VP6 surface for delivery of the encapsulated agent to a particular cell type. For example, antibodies reactive with tumor cell surface antigens can be easily associated with the VP6 sphere for the delivery of cytotoxic agents directly to tumor cells. Additionally, certain viral particles and other proteins are known to target particular cell and tissue types and these targeting agents can also be coupled to the VP6 sphere.

Targeting agents can be attached to the VP6 spheres either prior to or after the therapeutic agent is encapsulated, using conventional chemical coupling techniques. A particular advantage of the VP6 protein, however, is that this system facilitates the attachment of molecules with minimal manipulation, through protein-protein interactions. For example, a synthetic peptide corresponding to the targeting agent of interest can be chemically synthesized in such a way that it also contains an amino acid sequence (binding peptide) necessary to link it to VP6. The targeting agent can also be produced via recombinant DNA technology, as described above, in which case the nucleotide sequence corresponding to the binding peptide can be added so that the resulting product is a combination (fusion protein) of the targeting agent and the binding peptide. Attachment of the molecule to the VP6 carrier is then simply achieved by mixing the two substances without additional manipulation.

Several peptides have been found or designed that bind to VP6. The amino acid sequences for two are:

(1) Peptide A (22 amino acids): Cys-Asp-Gly-Lys-Tyr-Phe-Ala-Tyr-Lys-Val-Glu-Thr-Ile-Leu-Lys-Arg-Phe-His-Ser-Met-Tyr-Gly (SEQ ID NO:1), and (2) Peptide B (25 amino acids): Cys-Asn-Ile-Ala-Pro-Ala-Ser-Ile-Val-Ser-Arg-Asn-Ile-Val-Tyr-Thr-Arg-Ala-Gln-Pro-Asn-Gln-Asp-Ile-Ala (SEQ ID NO:2).

Both peptides A and B occur naturally as portions of virus protein 4 (VP4) of rotaviruses and are sensitive to trypsin. Cleavage of the peptides by trypsin prevents them from binding to VP6. It is clear that both of the sequences which are given herein are by way of example only, and that other compositions related to binding sequences, or sequences in which limited conservative amino acid changes are introduced, can also be used. Indeed additional binding peptides can be designed by those of skill in the art in light of the present disclosure. For example, variant peptides derived from peptide B can also be used, so long as the peptide includes a cysteine and positively charged amino acids and the three-dimensional conformation of the peptide are such that the peptide will bind to VP6. Such peptides are discussed further in copending U.S. patent application Ser. No. 07/489,790, filed 2 Mar. 1990, now U.S. Pat. No. 5,071,651.

VP6 spheres, so formed, containing biologically active agents, will find a variety of uses. Specifically, the effect and fate of the agent encapsulated within the VP6 sphere can be studied in vitro and systems for therapeutic use developed based on these findings.

Other uses include the treatment of a variety of disorders and diseases. As explained above, if a cytokine is encapsulated in the VP6 sphere, monocytes and macrophages can be activated, the immune system can be stimulated, and bacterial, viral, parasitic, and fungal infections fought. Furthermore, activated macrophages can also serve to retard tumor cell growth. Additionally, if a cytotoxic agent is encapsulated in the VP6 spheres and a targeting antibody directed against a tumor cell surface antigen present on the VP6 sphere, specific tumor cells can be targeted and acted upon by the cytotoxic agent present. Furthermore, as discussed above, other targeting agents can be coupled to the VP6 sphere to effect the delivery of particular drugs to specific cell or tissue types to elicit a local response.

VP6 spheres containing biologically active agents, either alone or in combination, can be formulated into pharmaceutical compositions for delivery to a desired host. The following modes of administration serve to deliver and combine the therapeutic agent to the selected group of cells in a mixture of cells. The preparation of such compositions is well understood in the art. Typically, pharmaceutical compositions for use with the instant invention are prepared as injectables, either as liquid solutions or suspensions. The preparation may also be emulsified. The VP6 encapsulated agent may be mixed with excipients which are pharmaceutically acceptable and compatible with the active ingredient. Suitable excipients are, for example, water, saline, dextrose, glycerol, ethanol, or the like, and combinations thereof. In addition, if desired, the pharmaceutical compositions may contain minor amounts of auxiliary substances such as wetting or emulsifying agents or pH buffering agents. The pharmaceutical compositions are conventionally administered parenterally, by injection, for example, either intravenously, subcutaneously or intramuscularly. Injectable formulations will contain an effective amount of the active ingredient, the exact amount being readily determined by one skilled in the art. The active ingredient can range from about 0.01% to about 95% (w/w) of the injectable composition, or even higher or lower if appropriate.

Controlled or sustained release formulations, known in the art, will also find use with the instant invention. Such formulations are described in, e.g., *Remington's Pharmaceutical Sciences,* Mack Publishing Company, Easton, Pa. (1985). VP6 with the therapeutic agent encapsulated therein can be combined with the particular sustained release formulation. Alternatively, the therapeutic agent to be delivered can be combined with the controlled release formulation and then encapsulated in the VP6 sphere.

Additional formulations which are suitable for other modes of administration include suppositories, in oral formulations and nasal aerosols. For suppositories, the pharmaceutical composition will include traditional binders and carriers, such as polyalkaline glycols, or triglycerides. Such suppositories may be formed from mixtures containing the active ingredient in the range of about 0.5% to about 10% (w/w), preferably about 1% to about 2%. Oral formulations include such normally employed excipients as, for example, pharmaceutical grades of mannitol, lactose, starch, magnesium, stearate, sodium saccharin cellulose, magnesium carbonate, and the like. These oral compositions may be taken in the form of solutions, suspensions, tablets, pills, capsules, sustained release formulations, or powders, and contain from about 10% to about 95% of the active ingredient, preferably about 25% to about 70%. Intranasal formulations for mammalian subjects will usually include vehicles that neither cause irritation to the nasal mucosa nor significantly disturb ciliary function. Diluents such as water, aqueous saline, or other known substances can be employed with the subject invention. The nasal formulations may also contain preservatives such as but not limited to chlorobutanol and benzalkonium chloride. A surfactant may be present to enhance absorption of the subject proteins by the nasal mucosa.

Furthermore, the VP6 encapsulated substances may be formulated into pharmaceutical compositions in either neutral or salt forms. If salts are used, the final preparation will typically contain less than 0.15M salt. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, or ferric hydroxides, and such organic bases as isopropylamine, trimethylamine, 2-ethylaminoethanol, histidine, procaine, and the like.

The formulations of the present invention may be administered in a manner compatible with the dosage formulation, and in such amounts as will be therapeutically effective. A "therapeutically effective amount" of a pharmaceutical composition is a dose sufficient to achieve the desired effect on the particular cell type in a subject to which the composition is administered. The dosages necessary to achieve these effects can be determined in view of this disclosure by one of ordinary skill in the art by running routine trials with appropriate controls. Comparison of the appropriate treatment groups to the controls will indicate whether a particular dosage is effective. In general, effective dosage will vary depending on the mode of administration. For example, in the case of an intramuscular injection, generally from 0.001 µg/kg to 10 µg/kg will find use in the instant invention.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR §1.14 and 35 USC §122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

| Strain | Deposit Date | ATCC No. |
| --- | --- | --- |
| pAC373BRV6 (in E. coli) | 31 August 1987 | 40362 |

C. EXPERIMENTAL

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See, Sambrook et al., supra. Restriction enzymes, $T_4$ DNA ligase, E. coli, DNA polymerase I, Klenow fragment, and other biological reagents were purchased from commercial suppliers and used according to the manufacturers' directions. Double-stranded DNA fragments were separated on agarose gels.

Cells and Virus

MA104 cells (African green monkey) were cultured in Eagle's minimal essential media (MEM) supplemented with 10% fetal bovine serum (FBS) (Gibco Laboratories, Grand Island, N.Y.). Bovine rotavirus isolate C486 was cultured from the feces of diarrheic calves by a method described previously (Babiuk, L. A. et al., *J Clin MiCrobiol* (1977) 6:610–617). Rotavirus C486 is publicly available from the ATCC, Rockville, Md. (accession no. VR-917).

The virus was propagated in confluent MA104 cells in the presence of 1 µg of trypsin (Difco Laboratories, Detroit, MI) per ml in the absence of FBS. Cells and supernatant were harvested together and cells were removed by centrifugation at 500 g for 20 min. Virus was concentrated from the clarified supernatant fluids by pelleting through a 40% sucrose-cushion at 100,000 g for 2½ hr at 15° C. The virus pellet was resuspended in double distilled water and the amount of virus protein was estimated spectrophotometrically as described previously (Ijaz, M. K. et al., *Antiviral Res* (1987) 8:283–298). The resuspended virus was stored at −70° C. The VP6 capsid protein was isolated from the preparation as described in the examples below.

Plaque Assay

A plaque assay for the quantitation of infectious rotavirus was performed according to the method described previously (Aha, P. M. and Sabara, M. I. *J Virol Methods* (1990) 28:25–32). Briefly, 12 well tissue culture plates (NUNC) containing confluent monolayers of MA104 cells, were washed twice with MEM (without FBS). Serial tenfold dilutions of each rotavirus isolate were prepared in MEM containing trypsin (Difco Laboratories, Detroit, Mich.) to a final concentration of 10 µg/ml. Following adsorption of the virus at 37° C. for 1 hr, the inoculum was aspirated, cells were washed with MEM and overlaid with Dulbecco's Modified Eagle Medium (DMEM), containing 4% Sephadex G-75 beads (Pharmacia). The plates were incubated for 2 days at 37° C., the overlay was aspirated and plates were stained with 0.5% crystal violet/80% methanol/PBS, washed and plaques enumerated.

Sodium Dodecyl Sulphate Polyacrylamide Gel Electrophoresis (SDS-PAGE)

Viral proteins were separated by SDS-PAGE under both reducing and non-reducing conditions according to the procedure described by Laemmli (Laemmli, U.K. *Nature* (1970) 227:680–685). Virus samples were resuspended in electrophoresis sample buffer (0.337M Tris pH 6.8, 6% SDS, 30% glycerol, 0.03% bromophenol blue) for running under nonreducing conditions and included 3.75% mercaptoethanol (BME) for reducing conditions. The samples were boiled for 5 to 10 min and analyzed following electrophoresis on a 10% polyacrylamide resolving gel with a 3% stacking gel.

Western Blotting of Rotavirus Proteins

Protein-specific antibodies were detected by the Western blotting technique described by Towbin et al. (Towbin, H. et al., *Proc Natl Acad Sci USA* (1979) 76:4350–4354). viral proteins separated on a 10% polyacrylamide gel, were transferred to nitrocellulose paper (0.45 μm) (BioRad Laboratories) by electroblotting at 100 volts for one hr in a buffer containing 20 mM Tris-190 mM glycine-20% methanol. Replica nitrocellulose strips were stained with amido black to determine the efficiency of protein transfer.

After transfer, reaction of viral protein with serum samples was determined as described previously (Braun, D. K. et al., *J Virol* (1983) 46:103–112). Nonspecific reactions were blocked with 3% bovine serum albumin (BSA) in 0.01M TBS. After washing with TBST, the reaction was developed with protein A gold (BioRad Laboratories) for one hr. Following development, the protein bands were intensified by silver enhancement (Janssen Biotech, N.V., Belgium).

EXAMPLE 1

Isolation of Native VP6

The VP6 viral protein was isolated from the purified virus suspension (described above) by successive degradation of purified virus with EDTA and either $CaCl_2$ or LiCl, as follows. Outer capsid proteins were removed by incubating virus (3 mg/ml) in 50 mM EDTA, 0.01M Tris-HCl, pH 7.4 at 4° C. for 30 min. Subviral particles were recovered by ultracentrifugation (100,000 xg, 2–3 hr, 4° C.) and resuspended in 0.01M Tris-HCl, pH 7.4 or 0.01M sodium borate, pH 9.0. They were then treated with either 1.5M $CaCl_2$ with 0.01M Tris-HCl, pH 7.4 at 20° C. for 20–30 min, or were frozen in 2M LiCl, 0.01M sodium borate, pH 9.0 at −70° C. for 4 days. Cores and undegraded particles were separated from solubilized protein by ultracentrifugation. EDTA and salts were removed by extensive dialysis at 4° C. against 0.01M Tris-HCl, pH 7.4, unless otherwise indicated. The purity of the samples was examined by polyacrylamide gel electrophoresis (PAGE) as described above.

EXAMPLE 2

Production of Recombinant VP6

The construction of recombinant Autographa californica nuclear polyhedrosis virus (AcNPV) containing gene 6 from bovine rotavirus (BRV) and assembly of VP6 particles following infection of spodoptera frugiperda (SF9) cells has been described previously (Redmond, M. J. et al., *Mol Immunol*, In Press). Briefly, genomic RNA extracted from purified bovine rotavirus strain C486 was used to produce cDNA. The cDNA was ligated into the Pst I site of pBR322 and used to transform *E. coli* strain DH1. The resulting colonies were probed with radiolabeled cDNA prepared from purified genomic RNA segment 6 as template.

Clone pR6-42 which contained a complete copy of the gene 6 RNA, was partially digested with Aha III which removed seven 5' noncoding nucleotides as well as the oligo-dC tails added during cDNA cloning. A Bam HI linker was then added.

The 3' oligo-dC tail and noncoding region were removed by digestion with Acc I which removes 56 noncoding nucleotides from the VP6 gene. A Bam HI linker was then added. The gene 6 cDNA was then ligated into the Bain HI site of the baculovirus transfer vector pac373. This vector was designated pAC373BRV6 (ATCC no. 40362). Integration of the rotavirus gene into the genome of *A. californica* was then carried out by homologous recombination in *S. frugidperda* (SF9) cells as outlined by Summers, M. D. and Smith, G. E., (1987) *Texas Agricultural Station Bulletin* 1555:26–27. Recombinants were identified by plaque hybridization, as described above, using radiolabeled cDNA prepared from purified genomic RNA segment 6. Recombinants were plaque purified and analyzed for expression of recombinant gene 6 produced proteins by SDS-PAGE analysis and Western blotting using the methods described above.

The recombinant virus containing gene 6 was used to infect SF9 cells. Following incubation for 72 hr at 27C, the cells were lysed in a 2 ml $NaHCO_3$ buffer (pH 7.5) containing 0.05% triton X-100 and 0.2 trypsin inhibitor units per ml. Cellular debris was removed by centrifugation at 1500 g. The supernatant was dialyzed against 0.1M glycine buffer (pH 3.0) for 24 hr. This dissociates VP6 aggregates into monomers. The dialysis solution was exchanged for 0.01M citrate buffer (pH 4.0) and dialysis continued for 24 hr, during which time spheres of VP6 formed. This dialysis buffer was exchanged for 0.01M citrate buffer (pH 5.0). Dialysis was then continued overnight at 4° C. Nonaggregated material was removed by ultracentrifugation using 300,000 dalton molecular weight cutoff filters. The quality of the VP6 spheres produced by this method was determined by electromicroscopy and purity confirmed by SDS-PAGE.

EXAMPLE 3

A. Encapsulation of Proteins of Varying Molecular Weights in VP6 Spheres

VP6 particles were produced as described in Example 2, with the following modifications. To a 1 ml sample containing VP6 (1 mg/ml), 200 μl of [$^{14}$C] methylated protein molecular weight markers (Table 1), in a solution containing a final concentration of 0.5% bovine serum albumin, were added to the VP6 preparation immediately before exchanging the glycine pH 3.0 buffer for the citrate pH 4.0 buffer and processing continued. To another 1 ml sample containing VP6 (1 mg/ml), 200 μl [$^{14}$C] methylated proteins were added to the VP6 preparation in 0.01M citrate pH 4.0 buffer and processing continued. Both samples were purified by centrifugation (100,000 g, 2 hr) through a 40% sucrose gradient. The pellets containing VP6 particles were resuspended in dd $H_2O$.

Protein analysis was carried out using SDS-Polyacrylamide gel electrophoresis and autoradiography. The results of this analysis indicated that [$^{14}$C] methylated protein molecular weight markers were encapsulated within the VP6 particle if added prior to sphere formation, i.e., at the pH 4.0 dialysis step. Little or no incorporation of the [$^{14}$C] methylated protein molecular weight markers was found if the proteins were added after particle formation, i.e., pH 5.0.

TABLE 1

Composition and Molecular Masses of Protein Standards

| Protein Identification | Apparent Molecular Mass |
|---|---|
| Myosin | 200,000 |
| Phosphorylase 6 | 97,400 |
| Bovine serum albumin | 69,000 |
| Ovalbumin | 46,000 |
| Carbonic anhydrase | 30,000 |
| Lysozyme | 14,300 |

B. Efficiency of Incorporation of Proteins

The efficiency of incorporation was monitored by adding 1 µCi of [$^{14}$C] methylated proteins prior to the 0.1 M citrate buffer pH 4.0 dialysis and proceeding with sphere formation as described previously. On completing the centrifugation through sucrose, the pellet containing the VP6 spheres was resuspended in dd H$_2$O and 3 replicate samples taken for radioactive content determination by liquid scintillation counting. Aliquots of the supernatant, containing the original sample buffer and sucrose, were also assayed in this manner. The results are shown in Table 2.

TABLE 2

Efficiency of the Protein Encapsulation Process

| Sample | Radioactivity (µCi) | % Incorporation |
|---|---|---|
| VP6 particles | 0.64 | 64 |
| Sucrose and supernatant | 0.02 | 2 |

As can be seen, VP6 particles were efficient in incorporating the tested proteins.

EXAMPLE 4

A. Encapsulation of Recombinant Human Gamma Interferon

The production of VP6 spheres proceeded as described in Example 2. For the purposes of encapsulation, dialysis against the pH 4.0 buffer was halted after 1 hour, and 10$^6$ units of recombinant human gamma interferon (rhu IFN) (Boehringer Mannheim Corp.) were added to the VP6 preparation. Dialysis was then resumed and allowed to continue overnight at 4° C. with 3 changes of pH 4.0 citrate buffer. The dialysis buffer was exchanged for 0.1 M citrate pH 5.0 and allowed to proceed for 24 hours with 3 changes of buffer.

B. Purification of VP6 Particles Containing Recombinant Human Gamma Interferon

The VP6 particles containing the rhu IFN were separated from free cytokine by centrifugation through a discontinuous sucrose gradient (40%, 60% steps; 100,000 g, 2 hrs). The pellet containing the VP6 particles was resuspended in 0.1 M citrate buffer pH 5.0 and stored frozen at −70 until use. SDS-PAGE analysis showed rhu IFN in the particles but none in the sucrose gradient.

EXAMPLE 5

Delivery and Functional Activity of Encapsulated rhu IFN

A. Isolation of peripheral blood mononuclear leukocytes (PBML)

Human PBML were obtained from 3 normal human donors: MC, MR, and HH. Blood from these donors was drawn into heparin-containing containers and centrifuged at 600 X g for 30 min. to obtain the buffy coat. Buffy coat cells were diluted 1:3 with Hanks' balanced salt solution (HBSS) and layered onto Ficoll-Hypaque (Pharmacia), density 1.077 g/cm$^3$ and the tubes were centrifuged at 800 X g for 45 min. Cells recovered from the interface were washed two times with HBSS and counted in trypan blue. Recovered cells were 98–100% mononuclear and 97–99% viable.

B. Culture and activation of PBML with rhu IFN and VP6-rhu IFN gamma preparations The culture media used throughout the experiments was RPMI 1640 supplemented with 10% FBS, 5 μg of gentamicin/ml, and 2 mM L-glutamine. In one experiment, PBML were resuspended in cultured media at 3 X $10^6$ cell/ml. Two ml of this cell suspension was dispensed into each well of 12-well tissue culture plates. In order to assess the activation properties of the VP6 encapsulated rhu IFN gamma, purified VP6, rhu IFN gamma, or VP6 containing rhu IFN gamma was added to different wells at the concentrations indicated in Table 3. These cultures were allowed to incubate for 18 hr at 37° C. in a humidified atmosphere of 95% air and 5% $CO_2$. After incubation, nonadherent cells were removed and adherent cells were recovered by lidocaine treatment (0.7% lidocaine for 10 min.). Nonadherent and adherent populations were pooled and stained for flow cytometric analysis and used for cytotoxic assays. In another experiment, cells were treated with the different activation protocols in 96-well plates at a concentration of $5\times10^5$ cells/well for cytotoxicity assays and $1\times10^6$ cells/well for flow cytometry.

C. Cytotoxicity assays

Microcytotoxicity assays were performed in triplicate in 96-well round-bottom microtiter plates. The nonadherent tumor target cells K562 (ATCC CCL 243) and P815 (ATCC TIB64) were labeled in suspension ($2\times 10^7$/ml) with 1 ml of RPMI 1640 containing 10% FBS and 100 μCi of $Na_2{}^{51}CrO_4$ for 2 hr at 37° C. Both target cells were washed three times in HBSS and resuspended at 2 X HBSS $10^5$ cell/ml. A 50 μl amount of cell suspension was added to each well containing effector cells and to wells containing media alone and 3% Triton X-100. The wells containing media alone served as spontaneous release controls, and the wells containing detergent served to calculate the total releasable $^{51}$Cr. Microtiter plates prepared in this way were incubated for 18 hr at 37° C in a humidified atmosphere of 95% air and 5% $CO_2$. After incubation, supernatant fluids were collected with a Titertek harvesting system (Flow Labs Inc.), and the amount of $^{51}$Cr released was counted in a gamma counter (Beckmann). Percentage cytotoxicity was defined as the amount of lysis for target cells in the presence of effector cells (PBML) minus the amount of lysis for target cells in the absence of effector cells and calculated based on the amount of $^{51}$Cr released as follows: % cytotoxicity=(mean CPM experiment-mean CPM spontaneous release)/(mean CPM total release-mean CPM spontaneous release). The percentage cytotoxicity is therefore a measure of the activation of effector cells by the tested lymphokines. The activated effector cells, in turn, kill the target cells tested. Non-activated effector cells lack the ability to kill the target cells tested. Results of the assays can be seen in Tables 3 and 4.

TABLE 3

Sample MC: Effect of different activation protocols on cytotoxic function

| | % Cytotoxicity[a] | |
|---|---|---|
| Treatment | K562 | P815 |
| control | 12.2 | 4.1 |
| IL-2 10 units[b] | 19.5 | 8.7 |
| VP6 1:100 | 11.4 | 0.8 |
| VP6 1:1000 | 9.9 | 2.7 |
| VP6 1:10000 | 11.3 | 2.9 |
| VP6-rhuIFN | | |
| 1:100 | 17.7 | 13.8 |
| 1:1000 | 16.2 | 7.8 |
| 1:10000 | 10.4 | 8.7 |
| rhuIFN | | |
| 1000 units | 17.4 | 12.8 |
| 100 units | 13.5 | 7.2 |
| 10 units | 10.4 | 7.8 |

[a]Percentage cytotoxicity was assessed as described in Example 5C. The effector:target cell ratio for this experiment was 10:1.
[b]recombinant human IL-2 was used as positive control for enhancement of cytotoxicity.

TABLE 4

Donors MR and HH: Effect of VP6 and VP6-IFN treatments on cyctotoxic function

| | % Cytotoxicity vs. P815 cells[a] | |
|---|---|---|
| Treatment | donor MR | donor HH |
| Control | 1.8 | 4.2 |
| HuIL-2 | 47.8 | 30.4 |
| VP6 | 5.7 | 3.8 |
| VP6-rhuIFN | 28.6 | 10.7 |
| rhuIFN | 23.6 | 8.6 |

[a]Cytotoxicity was assessed as described above. The effector:target cell ratio for this experiment was 50:1. Donors MR and HH were human subjects.

As can be seen, the encapsulated lymphokines were effective in activating effector cells which in turn killed the target cells tested.

D. Assessment of MHC class II antigen expression

Another way of assessing cell activation and thus effective delivery of the tested lymphokines is by measuring the expression of MHC class II surface antigens since activated cells show increased expression of the same.

PBML were assayed for surface expression of MHC class II antigen expression by direct fluorescent flow cytometry. Increased peak fluorescence indicates the presence of increased MHC class II antigen expression. Following activation and recovery of adherent cells, PBML were washed twice in HBSS and resuspended in PBS with 0.5% gelatin and 0.02 M $NaN_3$. PBML were incubated in ice for 1 hr in the presence of FITC-labeled monoclonal antibodies against MHC Class II molecules (Becton Dickinson). After incubation, PBML were washed three times in PBS/gelatin and fixed in 0.4% paraformaldehyde in 0.1 M PBS, pH 7.1. Flow cytometric analysis was performed on $5\times10^3$ cell per sample with the aid of a Coulter Electronics Ltd. Epics V flow cytometer. Data were collected on logarithmic amplification in one parameter analysis. Increased fluorescence intensity was used to assess the ability of different treatment protocols to enhance MHC class II expression, and it was expressed as the histogram channel where peak fluorescence for a given sample was observed. The proportion of cells expressing MHC class II antigens were expressed as the percentage of positive cells. Results can be seen in Tables 5 and 6.

TABLE 5

Sample MC: Assessment of MHC class II expression by flow cytometry

| | Fluorescence using FITC-labeled anti-HLA-DR | |
|---|---|---|
| Treatment | % positive cells | peak channel fluorescence |
| control | 23.9 | 110 |
| VP6 1:100 | 21.6 | 124 |
| VP6 1:1000 | 19.4 | 109 |
| VP6 1:10000 | 20.4 | 103 |
| VP6-rhuIFN | | |
| 1:100 | 23.2 | 157 |
| 1:1000 | 20.9 | 145 |
| 1:10000 | 18.5 | 131 |
| rhuIFN | | |
| 1000 units | 24.8 | 128 |
| 100 units | 19.9 | 118 |
| 10 units | 23.3 | 105 |

TABLE 6

Donors MR and HH: Assessment of MHC class II expression by flow cytometry

| | | Fluorescence using FITC-labeled anti-HLA-DR | |
|---|---|---|---|
| Donor | Treatment | % positive cells | peak channel fluorescence |
| MR | control | 30.6 | 93 |
| MR | VP6 | 29.4 | 104 |
| MR | VP6-rhuIFN | 32.2 | 151 |
| MR | rhuIFN | 31.5 | 142 |
| HH | control | 32.6 | 106 |
| HH | VP6 | 34.6 | 113 |
| HH | VP6-rhuIFN | 34.1 | 159 |
| HH | rhuIFN | 32.4 | 141 |

As can be seen in the tables, peak fluorescence was increased in the VP6 encapsulated interferon group as compared to controls or VP6 without encapsulated interferon, indicating cell activation and thus delivery.

EXAMPLE 6

Encapsulation of Recombinant Bovine IL-2 in VP6 Spheres

The production of VP6 spheres proceeeded as described in Example 2. For the purposes of encapsulation, dialysis against the pH 4.0 buffer was halted after 1 hour, and 0.1 mg of recombinant bovine IL-2 (rBoIL-2) was added to each 1.0 mg of VP6. Dialysis was then resumed and allowed to continue for 90 minutes at 4° C. with 3 changes of citrate buffer. The dialysis was exchanged for citrate pH 5.0 and allowed to proceed for 24 hours with 3 changes of buffer.

The VP6 particles were then separated form free cytokine by centrifugation through sucrose as described in example 4B. The quantity of rBoIL-2 encapsulated was assessed by Western blotting samples of rBoIL-2— VP6 and quantitated amounts of rBoIL-2, and probing with IL-2 specific antisera followed by visualization of antibody binding using protein A—gold. The blot was then scanned and the amount of encapsulated rBoIL-2 estimated by reference to the rBoIL-2 standards.

EXAMPLE 7

Delivery and Functional Activity of Recombinant Bovine IL-2

A. Isolation of Peripheral Blood Mononuclear Cells from Bovine Blood

Bovine PBML were obtained from a normal bovine donor. The blood was drawn into heparin-containing tubes and centrifuged at 600 x g for 30 min. to obtain the buffy coat. Buffy coat cells were diluted 1:3 with Hank's balanced salt solution (HBSS) and layered onto Ficoll-Hypaque, density 1,077 g/cm$^3$ and the tubes were centrifuged at 800 x g for 45 min. Cells were recovered from the interface and washed twice with HBSS and counted in trypan blue. Recovered cells were typically 98–100% mononuclear cells and 97–99% viable.

B. Culture and Activation of PBML with rBoIL-2 and VP6 —rBoIL-2 Preparations

The culture media used throughout the experiments was RPMI 1640 supplemented with 10% FBS, 5ug of gentamycin/ml, and 2mM L-glutamine. The PBML's were resuspended in media at an initial concentration of 2× 10$^6$ cells/ml and distributed in 100 ul aliquots into a 96 well tissue-culture plate. The cells were then incubated for 72 hours in the presence of quantitated amounts of rBoIL-2,VP6 —rBoIL-2, VP6 or media control as shown in Table 7. Each sample was represented by three wells. After 72 hours, tritiated thymidine was added to all of the wells and incubation was continued for 16 hours. At this time, the cells were harvested and the incorporation of radiolabel assessed. All results are the mean of triplicate wells and are expressed as a proliferation index according to the formula:

(Test CPM)/(Media control CPM).

The results of this experiment indicate that not only is the VP6 encapsulated rBoIL-2 biologically active but it produces an in-vitro dose response curve consistent with free rBoIL-2.

TABLE 7

|  | CPM |
|---|---|
| rBoIL-2 Control | |
| 1000 ng | 39247 |
| 333 | 37247 |
| 111 | 26901 |
| 37 | 24426 |
| 12 | 21299 |
| 4 | 18696 |
| 1.4 | 15159 |
| 0.46 | 8866 |
| 0.15 | 5281 |
| rBoIl-2 - VP6 | |
| 2000 ng | 25322 |
| 200 | 21965 |
| 100 | 22769 |
| 50 | 17199 |
| 25 | 14664 |
| 12.5 | 9552 |
| 6.25 | 5207 |
| 3.1 | 3330 |
| 1.6 | 2557 |
| 0.78 | 1761 |
| 0.39 | 1268 |
| VP6 control | |
| 10 ul | 1035 |
| 5 | 1284 |
| Media | 1494 |
|  | 1476 |
|  | 1043 |
|  | 1038 |

Thus, the production of VP6 encapsulated biologically active agents is disclosed. Although preferred embodiments of the subject invention have been described in some detail, it is understood that obvious variations can be made without departing from the spirit and the scope of the intention as defined by the appended claims.

We claim:

1. A composition of matter which comprises oligomeric spherical particles of rotavirus VP6 protein, said particles having encapsulated therein at least one biologically active protein or peptide having a molecular weight of at least 14.3 KD, wherein said protein or peptide is other than a rotavirus component.

2. The composition of claim 1 wherein said protein is selected from the group of γ-interferon and interleukin-2.

3. A method to encapsulate a biologically active protein or peptide in oligomeric spherical particles of rotavirus VP6 protein, which method comprises mixing monomeric VP6 protein with said biologically active protein or peptide at a pH of about 3; and effecting the formation of oligomeric spheres of rotavirus VP6 in the presence of said biologically active protein or peptide at about pH 4, and thereby encapsulating at least some of said biologically active protein or peptide; and separating the encapsulated biologically active protein or peptide from any unencapsulated biologically active protein or peptide.

\* \* \* \* \*